US008137736B2

(12) United States Patent
Zhu et al.

(10) Patent No.: US 8,137,736 B2
(45) Date of Patent: Mar. 20, 2012

(54) FABRICATION METHOD FOR HOLLOW MICRONEEDLES FOR DRUG DELIVERY

(75) Inventors: Mingwei Zhu, Nanjing (CN); Yanfeng Chen, Nanjing (CN); Zhenlin Wang, Nanjing (CN); Yanqing Lu, Nanjing (CN); Haixiong Ge, Nanjing (CN); Yuefeng Tang, Nanjing (CN)

(73) Assignee: Nanjing University, Nanjing (CN)

( * ) Notice: Subject to any disclaimer, the term of this patent is extended or adjusted under 35 U.S.C. 154(b) by 526 days.

(21) Appl. No.: 12/348,589

(22) Filed: Jan. 5, 2009

(65) Prior Publication Data

US 2010/0062142 A1  Mar. 11, 2010

(30) Foreign Application Priority Data

Sep. 9, 2008  (CN) .......................... 2008 1 0196403

(51) Int. Cl.
*B05D 3/12* (2006.01)
(52) U.S. Cl. .......................... 427/2.3; 604/191; 604/272
(58) Field of Classification Search ................... 427/2.3; 604/191, 272
See application file for complete search history.

(56) References Cited

U.S. PATENT DOCUMENTS

| | | | | |
|---|---|---|---|---|
| 6,334,856 B1 * | 1/2002 | Allen et al. | ................... | 604/191 |
| 2003/0111759 A1 * | 6/2003 | Wood et al. | ................... | 264/131 |

OTHER PUBLICATIONS

Mark R. Prausnitz, "Microneedles for transdermal drug delivery", Advanced Drug Delivery Reveiw, 2004, 56: 581-587.
Wermeling, et al. "Microneedles permit transdermal delivery of a skin-impermeant medication to humans", Proceedings of the National Academy of Sciences, Feb. 12, 2008, vol. 105, No. 6, pp. 2058-2063.
McAllister, et al. "Microfabricated needles for transdermal delivery of macromolecules and nanoparticles: Fabrication methods and transport studies" Proceedings of the National Academy of Sciences, Nov. 25, 2003, vol. 100, No. 24, pp. 13755-13760.
Gardeniers, et al. "Silicon micromachined hollow microneedles for transdermal liquid transport", Journal of Microelectromechanical Systems, vol. 12, Issue 6, Dec. 2003, pp. 855-862. Abstract only.
Davis, et al. "Hollow Metal Microneedles for Insulin Delivery to Diabetic Rats", IEEE Transactions on Biomedical Engineering, vol. 52, No. 5, May 2005, pp. 909-915.
Stoeber, et al., "Arrays of Hollow Out-of-Plane Microneedles for Drug Delivery", Journal of Microelectromechanical Systems, vol. 14, No. 3, Jun. 2005, pp. 472-479.
Ovsianikov, et al. "Two photon polymerization of polymer-ceramic hybrid materials for transdermal drug delivery", International Journal of Applied Ceramic Technology vol. 4, No. 1, pp. 22-29, 2007.
Perennes, et al. "Sharp beveled tip hollow microneedle arrays fabricated by LIGA and 3D soft lithography with polyvinyl alcohol", Journal of Micromechanics and Microengineering, vol. 16, pp. 473-479, 2006.
Huang, et al. "Different fabrication methods of out-of-plane polymer hollow needle arrays and their variations", Journal of Micromechanics and Microengineering, vol. 17, pp. 393-402, 2007.
Ji, et al. "Microfabricated Hollow Microneedle Array Using ICP Etcher", Journal of Physics: Conference Series 34, pp. 1132-1136, 2006.
Lopez, et al. "Focused ion beam-assisted technology in sub-picolitre micro-dispenser fabrication" Journal of Micromechanics and Microengineering vo.18, 075021, pp. 1-8, 2008.
Xia, et al. "Unconventional methods for fabricating and patterning nanostructures", Chemical Reviews, vol. 99, No. 7, pp. 1823-1848, 1999.

\* cited by examiner

*Primary Examiner* — Peter Szekely
(74) *Attorney, Agent, or Firm* — Chen Yoshimura LLP

(57) ABSTRACT

A novel method suitable for commercially mass production of hollow microneedle with high quality for delivery of drugs across or into biological tissue is provided. It typically includes the following processes: (1) coating an elongated template of a first material with a second material to form a cover; (2) removing tips of the template and cover to form an opening in the cover; and (3) removing the template of the first material to obtain hollow microneedles of the second material. This simple, efficient and cost-effective fabrication method can mass produce hollow microneedle arrays involving no complicated and expensive equipments or techniques, which can be used in commercial fabrication of hollow needles for delivering drugs or genes across or into skin or other tissue barriers with advantages of minimal damage, painless, long-term and continuous usages.

8 Claims, 2 Drawing Sheets

FABRICATION METHOD FOR HOLLOW MICRONEEDLES FOR DRUG DELIVERY

BACKGROUND OF THE INVENTION

1. Field of the Invention

This invention relates to hypodermic needles. More particularly, the invention relates to microneedles and fabrication methods thereof.

2. Description of the Related Art

Transdermal drug delivery represents a novel drug delivery route with little damage or pain. Such a drug delivery method has overcome the shortcomings in oral route that the drugs may be degraded in the gastrointestinal tract or be eliminated through the liver. Hence it has now been widely recognized as one of the most promising techniques with numerous commercial applications. The outer layer of skin (stratum corneum) is the most important barrier that prevents the drugs entering into the body. How to break through the stratum corneum painlessly and effectively is the key technique in transdermal drug delivery. Among the transdermal drug delivery techniques, hollow microneedle arrays have now been widely recognized as one of the most promising techniques. It can deliver drugs by painlessly piercing through the stratum corneum without reaching the dermis layer. Compared with methods of ion-implantation and electroporation, the holes throughout the stratum corneum generated by microneedles are much bigger and can delivery macromolecules, super-molecules, or even the particles into the body. Therefore, the fabrication methods for microneedles remain a hotspot research area in recent years. In the early stage, the fabricated microneedles are solid ones and can let the drugs diffuse into the body by generating holes in the skin. Recently, hollow microneedles are proposed for their advantages of the combination of microneedles and drug delivery. The drugs can be delivered into the skin through the tunnels existing in the hollow microneedles, which can greatly improve the efficiency of drug delivery and instantly control the drug species as well as their dosages painlessly and conveniently. However, the fabrications of hollow microneedle arrays mainly relied on the microfabrication techniques of a modified-LIGA process, a combination of deep reactive ion etching (RIE) and isotropic etching techniques, femtosecond laser two photon polymerization, deep x-ray lithography (DXRL) process, photo lithography, inductively coupled plasma (ICP) etcher, focused ion beam (FIB)-assisted technology, etc. In these cases, achieving commercial mass production of hollow microneedle arrays have been hindered greatly mainly by the inherent high cost and low throughput of the existing fabrication methods. Usually, the cost originated from microfabrication processes can be shared by many replicas to ensure the overall low cost. But this case was no longer effective for fabrication of hollow microneedle arrays using the current methods, because the mold had to be sacrificed during the fabrication processes and each mold can be used for only one time. Moreover, the hollow microneedles can be used for only one time to avoid cross infection and contamination. Up to now, it still remains a great challenge to fabricate hollow microneedle arrays efficiently and cost-effectively by commercially mass production, which greatly restricts their applications.

SUMMARY OF THE INVENTION

Accordingly, the present invention is directed to a hollow microneedles and fabrication method thereof that substantially obviates one or more of the problems due to limitations and disadvantages of the related art.

An object of the present invention is to provide a simple method for fabricating hollow microneedles.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

The fabrication method mainly includes processes of (1) coating an elongated template made of a first material with a second material to form a cover; (2) removing a tip of the cover and the template to form an opening in the cover; and (3) removing the template, whereby the cover with the opening forms a hollow microneedle.

The fabrication methods have the following advantages: it can mass produce hollow microneedles; it involves no complicated and expensive equipments or techniques; the quality of the resulted needles is very high; the investment on both fabrication equipments and materials is very low.

The above advantages may enable the fabrication method preponderant among all of the present hollow microneedles fabrication methods.

It is to be understood that both the foregoing general description and the following detailed description are exemplary and explanatory and are intended to provide further explanation of the invention as claimed.

DETAILED DESCRIPTION OF THE PREFERRED EMBODIMENTS

Figure 1:
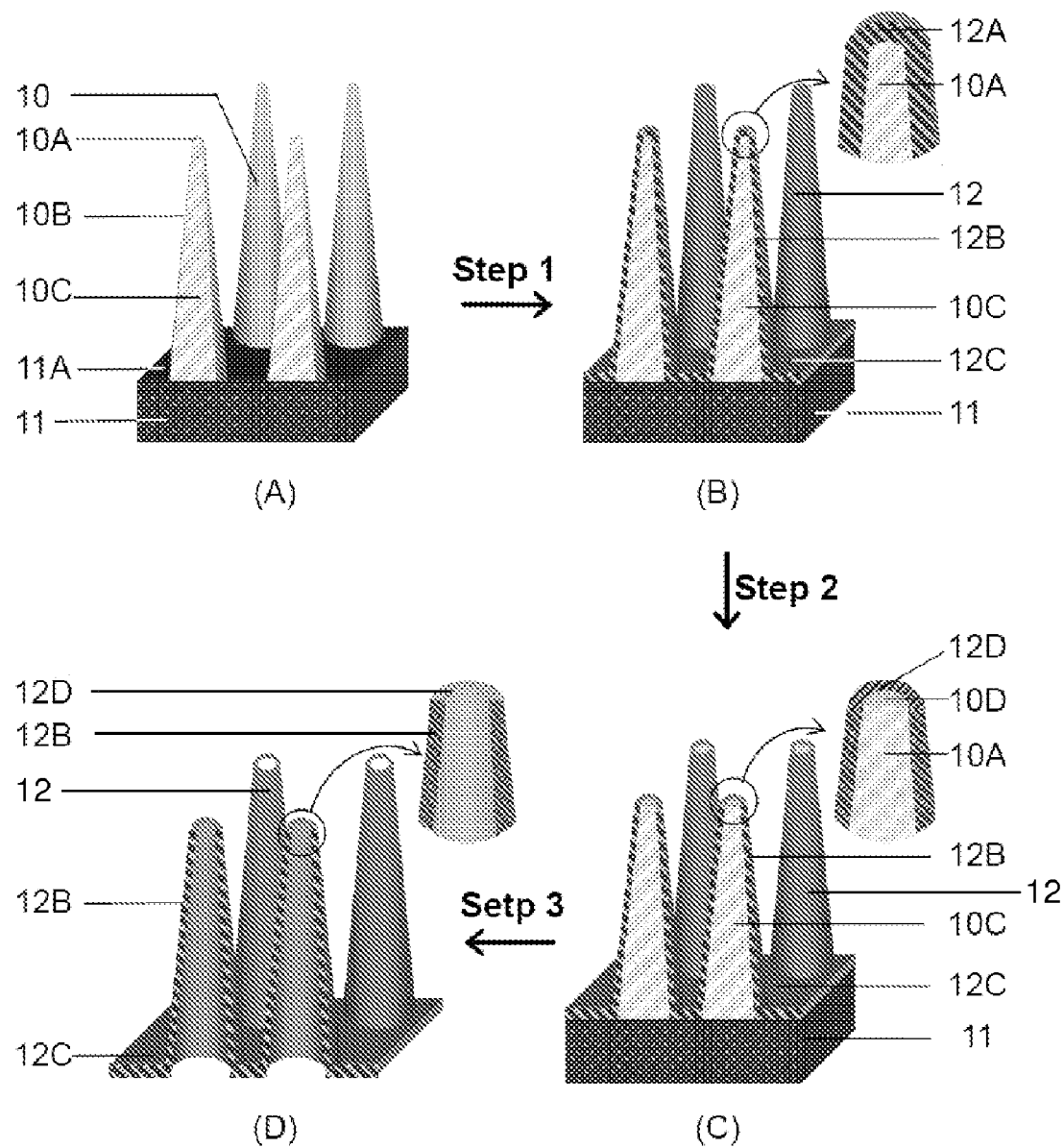
FIGS. 1(A) to 1(D) schematically illustrate a hollow microneedle fabrication process according to an embodiment of the present invention.

The preferred embodiments of the invention will be described more fully hereinafter referencing to the accompanying schematic drawings. Before the present invention is described, it is to be understood that, this invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the thickness of layers and regions are exaggerated for clarity.

FIGS. 1(A) to 1(D) schematically illustrate a hollow microneedles fabrication process according to an embodiment of the present invention. As illustrated, the process includes three steps. Step (1): coating templates of a first material with a second material using techniques including but not limited to painting, spin-coating, sputtering, pulling, electroless plating, electroplating, physical vapor deposition, chemical vapor deposition, sol-gel, or their combinations. Step (2): The tips of the resulting structures are partly removed by methods including but not limited to cutting, shearing, polishing, etching, reactive ion etching, focused ion beam irradiation, lithography, laser irradiation, or their combinations. Step (3): The original templates of the first material are removed by methods including but not limited to sintering, dissolving, melting, etching, or their combinations. The fabrication process is described in more detail below.

FIG. 1(A) is a partial cut-away view illustrating the template needles 10 before Step 1 (the coating step). In Step 1, a surface coating process is used to cover the needles 10 on their surfaces of needle tips 10A, the surfaces of needle sides 10B, and the substrate 11 on their top surface 11A. The coating methods, not listed all here, may be selected from methods of painting, spin-coating, sputtering, pulling, electroless plating, electroplating, physical vapor deposition, chemical vapor deposition, sol-gel, or their combinations. The shape of the template needles 10 is generally elongated, and may be cones, columns, or other more complicated shapes. The material of the template needles may be inorganic materials, or organic materials, or metals, or their combinations. The materials of the needles 10 and the substrate 11 may be the same. The coating material may be inorganic materials, or organic materials, or metals, or their combinations, but it is different from the material of the template needles 10. Although the term "material" is used in this disclosure in its singular form, it should be understood that the material of the template and the material of the coating can be mixtures of materials or composite materials. The result of the coating step is schematically shown in FIG. 1(B). The coating material forms needle covers 12 with tips 12A, sidewall 12B, and base 12C. The covering thicknesses of the coating material as indicated in FIG. 1(B) can be adjusted in a range of approximately 20 nm to 500 μm.

In Step 2, the tips 12A of the needle covers 12 and tips 10A of the template needles 10 are removed. The removal method may be selected from cutting, shearing, polishing, etching, reactive ion etching, focused ion beam irradiation, lithography, laser irradiation, or their combinations, but not list all here. As schematically shown in FIG. 1(C), the material coating the surfaces of template needles 10 and the substrate 11A forms nanostructures with through holes filled with template needles 10C. In this process, openings 12D of the needle covers 12 are generated. The sizes of the openings 12D can be adjusted by the height of the tips 12A and 10A that are removed.

Then, in Step 3, the template 10 and substrate 11 are removed to form hollow microneedles 12. The removal methods may be selected from sintering, dissolving, melting, etching, or their combinations, but they are not all listed here. After this process, as shown in FIG. 1(D), the hollow needles 12 are formed, each hollow needle including an opening 12D and a side wall 12B. The hollow needle array also includes abase 12C joining the hollow needles.

Accordingly, the hollow microneedles fabrication method enables fabrication of hollow microneedle arrays with very high quality in an extremely cheap and efficient way. It can use microfabrication-free techniques, materials of metals and/or polymers, as described above, which has great flexibilities and be suitable for both lab and industry mass production of hollow microneedles.

Figure 2:
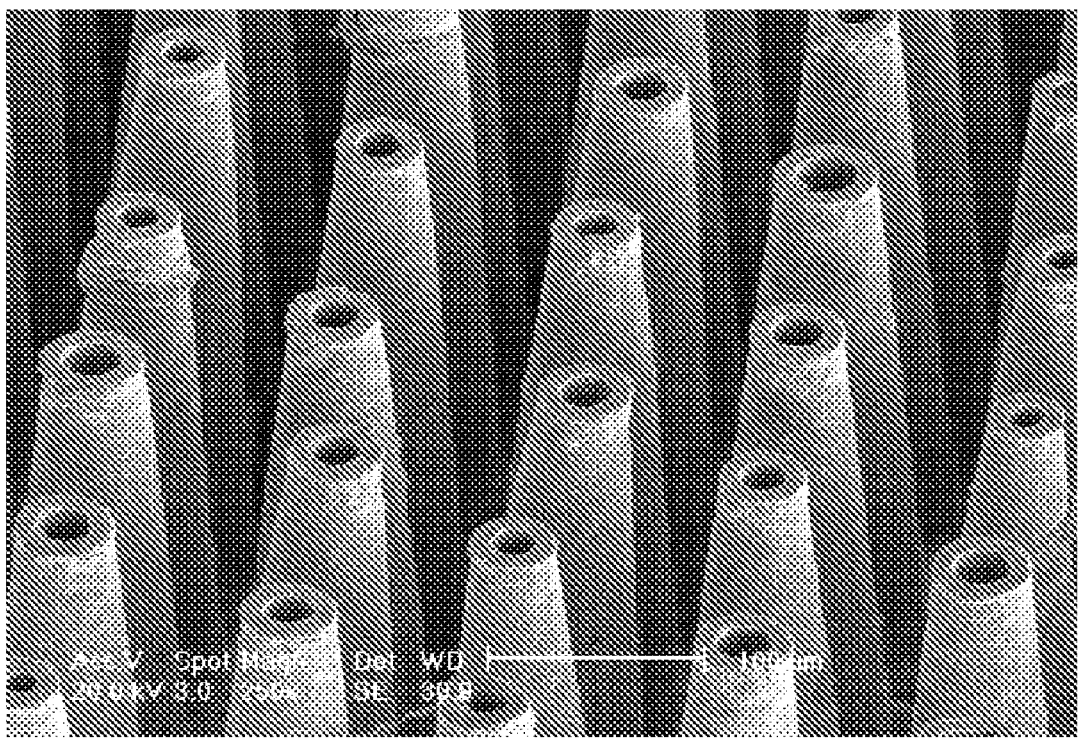
FIG. 2 is a scanning electron microscope (SEM) image of a hollow microneedle array fabricated using a method according to an embodiment of the present invention.

FIG. 2 is a scanning electron microscope (SEM) image of a hollow needle array fabricated using a preferred embodiment of the present invention. The resulting nickel hollow microneedles have a height of about 300 μm, a wall thickness of about 10 μm, and an opening diameter of about 20 μm.

A number of specific examples of the microneedle fabrication process are described below.

EXAMPLE 1

A layer of copper with thickness of about 50 μm is electroplated on the surface of poly(methyl methacrylate) (PMMA) microneedles array of 500 μm in diameter for a single needle, then the tips of the needles are removed by about 100 μm in length by cutting. Finally, the PMMA is removed by immersing in trichloromethane for about 2 hours, which results in a copper hollow microneedles array.

EXAMPLE 2

A layer of gold with thickness of about 20 nm is sputtered on the surface of silica microneedles array of 3 μm in diameter for a single needle, then the tips of the needles are removed by about 50 nm in length by etching. Finally, the silica is removed by immersing in hydrofluoric acid for about 60 min, which results in a gold hollow microneedles array.

EXAMPLE 3

A layer of polystyrene with thickness of about 500 μm are directly coated on the surface of iron microneedles array of 2 mm in diameter for a single needle, then the tips of the needles are removed by about 1 mm in length by cutting. Finally, the iron is removed by immersing in hydrochloric acid for about 1 min, which results in a polystyrene hollow microneedles array.

EXAMPLE 4

A layer of nickel with thickness of about 10 μm is electroplated on the surface of poly(methyl methacrylate) (PMMA) microneedles array of 100 μm in diameter for a single needle, then the tips of the needles are removed by about 50 μm in length by polishing. Finally, the PMMA is removed by sintering at 400° C. for about 1 hour, which results in a nickel hollow microneedles array.

EXAMPLE 5

A layer of PZT ceramic with thickness of about 50 μm is sputtered on the surface of poly(methyl methacrylate) (PMMA) microneedles array of 500 μm in diameter for a single needle, then the tips of the needles are removed by about 100 μm in length by polishing. Finally, the PMMA is removed by immersing in trichloromethane for about 2 hours, which results in a ceramic hollow microneedles array.

EXAMPLE 6

A layer of gold with thickness of about 1 μm is electroless plated on the surface of silicon microneedles array of 10 μm in diameter for a single needle, then the tips of the needles are removed by about 10 μm in length by polishing. Finally, the silicon is removed by immersing in KOH solution for about 2 hours, which results in a gold hollow microneedles array.

EXAMPLE 7

A layer of poly(methyl methacrylate) (PMMA) with thickness of about 10 μm is electroless plated on the surface of silica microneedles array of 200 μm in diameter for a single needle, then the tips of the needles are removed by about 50 μm in length by cutting. Finally, the silica is removed by immersing in HF solution for about 2 hours, which results in a PMMA hollow microneedles array.

EXAMPLE 8

A layer of silica with thickness of about 10 μm is sol-gel coated on the surface of polystyrene (PS) microneedles array of 50 μm in diameter for a single needle, then the tips of the needles are removed by about 20 μm in length by polishing. Finally, the PS is removed by sintering at 400° C. for about 1 hour, which results in a silica hollow microneedles array.

EXAMPLE 9

A layer of silver with thickness of about 100 nm is electroless plated on the surface of poly(methyl methacrylate) (PMMA) microneedles array of 3 μm in diameter for a single needle, then holes are generated on the tips of the needles by laser drilling. Finally, the PMMA is removed by immersing in trichloromethane for about 1 hour, which results in a silver hollow microneedles array.

EXAMPLE 10

A layer of nickel with thickness of about 10 μm is electroplated on the surface of polystyrene (PS) microneedles array of 300 μm in diameter for a single needle, then holes are generated on the tips of the needles with focused ion beam. Finally, the PS is removed by sintering at 400° C. for about 1 hour, which results in a nickel hollow microneedles array.

In the drawings and specification, there have been disclosed typical preferred embodiments of the invention and, although specific terms are employed, they are used in a generic and descriptive sense only and not for purposes of limitation. It will be apparent to those skilled in the art that various modification and variations can be made in the hollow microneedles fabrication processes of the present invention without departing from the spirit or scope of the invention. Thus, it is intended that the present invention cover modifications and variations that come within the scope of the appended claims and their equivalents.

What is claimed is:

1. A method for fabricating a hollow microneedle comprising:
    (1) coating an elongated template made of a first material with a second material to form a cover;
    (2) removing a tip of the cover and a tip of the template to form an opening in the cover, wherein the tip of the cover and the tip of the template are removed in a single step; and
    (3) removing a remaining portion the template, whereby the cover with the opening forms a hollow microneedle.

2. The method of claim 1, wherein in step (1) the first material includes inorganic materials, or organic materials, or metals, or their combinations.

3. The method of claim 1, wherein in step (1) a shape of the template includes cones or columns.

4. The method of claim 1, wherein in step (1) the coating is performed by painting, spin-coating, sputtering, pulling, electroless plating, electroplating, physical vapor deposition, chemical vapor deposition, sol-gel, or their combinations.

5. The method of claim 1, wherein in step (1) the second material includes inorganic materials, or organic materials, or metals, or their combinations, and wherein the second material is different from the first material.

6. The method of claim 1, wherein in step (1) a thickness of the cover is about 20 nm to 500 μm.

7. The method of claim 1, wherein in step (2) the removing is performed by cutting, shearing, polishing, etching, reactive ion etching, focused ion beam irradiation, lithography, laser irradiation, or their combinations.

8. The method of claim 1, wherein in step (3) the removing is performed by sintering, dissolving, melting, etching, or their combinations.

* * * * *